United States Patent
Toda et al.

(10) Patent No.: US 7,384,627 B2
(45) Date of Patent: Jun. 10, 2008

(54) ANTITUMOR AGENTS WITH THE USE OF HSV

(75) Inventors: Masahiro Toda, Kanagawa (JP); Yutaka Kawakami, Kanagawa (JP); Yukihiko Iizuka, Rockville, MD (US); Yoko Ueda, Kanagawa (JP); Yoshihiro Iwahori, Tokyo (JP)

(73) Assignee: Institute of Gene and Brain Science, Tokyo (JP)

(*) Notice: Subject to any disclaimer, the term of this patent is extended or adjusted under 35 U.S.C. 154(b) by 80 days.

(21) Appl. No.: 10/513,193

(22) PCT Filed: May 2, 2003

(86) PCT No.: PCT/JP03/05626

§ 371 (c)(1),
(2), (4) Date: Jun. 3, 2005

(87) PCT Pub. No.: WO03/092708

PCT Pub. Date: Nov. 13, 2003

(65) Prior Publication Data

US 2005/0249705 A1    Nov. 10, 2005

(30) Foreign Application Priority Data

May 2, 2002   (JP)  ............................. 2002-130954
Jul. 15, 2002  (JP)  ............................. 2002-206291
Oct. 31, 2002  (JP)  ............................. 2002-319157

(51) Int. Cl.
  *A61K 49/00*  (2006.01)
  *A61K 39/245*  (2006.01)
(52) U.S. Cl. .................... 424/93.1; 424/229.1
(58) Field of Classification Search ............. 424/229.1, 424/93.1
  See application file for complete search history.

(56) References Cited

U.S. PATENT DOCUMENTS 5,851,533 A * 12/1998 Berman et al. ........... 424/229.1
7,264,817 B1 * 9/2007 Berman et al. ........... 424/229.1

FOREIGN PATENT DOCUMENTS

| WO | WO 85/04587 | 10/1985 |
| WO | WO 90/06756 | 6/1990 |
| WO | WO 93/19591 | 10/1993 |
| WO | WO 96/03997 | 2/1996 |
| WO | WO 96/39841 | 12/1996 |
| WO | WO 99/07394 | 2/1999 |
| WO | WO 99/40938 | 9/1999 |
| WO | WO 00/08191 | 2/2000 |
| WO | WO 00/40734 | 7/2000 |
| WO | WO 00/45853 | 8/2000 |
| WO | WO 00/75292 | 12/2000 |
| WO | WO 01/09361 | 2/2001 |
| WO | WO 01/19380 | 3/2001 |
| WO | WO 01/26681 | 4/2001 |
| WO | WO 01/41801 | 6/2001 |
| WO | WO 01/91789 | 6/2001 |
| WO | WO 01/53505 | 7/2001 |
| WO | WO 01/53506 | 7/2001 |
| WO | WO 01/77358 | 10/2001 |

OTHER PUBLICATIONS

Dupuis et al. Vaccine 2000, vol. 18, pp. 434-439,.*
Ankel et al. Virol. 1998, vol. 251, pp. 317-326.*
Rosenthal et al. J. Virol. 1987, vol. 61, No. 8, pp. 2438-2447.*
Keadle et al. J. Infec. Dis. 1997, vol. 176, pp. 331-338.*
Walker et al. (Human Gene Therapy 1999, vol. 10, No. 13, pp. 2237-2243.*
Cinatl et al. Cancer Research Apr. 2003, vol. 63, pp. 1508-1514.*
Stanberry et al. The New England Jouranl of Medicine, Nov. 2002, vol. 21, pp. 1652-1661.*
Endo, Takashi et al., "Cancer Vaccination Therapy for the Liver Metastasis of Colon Cancer," Nihongangakkai Sokai Kiji, 2001, vol. 60, p. 621 (Japanese abstract No. 2182 *with Translation*).
Toda, Masahiro et al.; "In situ cancer vaccine therapy for metastatic tumors"; Neuroimmunological Research, 1999; vol. 12, pp. 181-185 (*with Translation*).
Boon, Thierry et al., "Tumor Antigens Recognized By T Lymphocytes," Annu. Rev. Immunol. 1994, vol. 12, pp. 337-365.
Brandt, Curtis et al., "Treatment of Spontaneously Arising Retinoblastoma Tumors in Transgenic Mice with an Attenuated Herpes Simplex Virus Mutant," Virology, 1997, vol. 229, pp. 283-291.
Dranoff, Glenn et al., Gene Transfer as Cancer Therapy, Advances in Immunology, vol. 58, pp. 417-455.
Endo, Takashi et al.; "Therapeutic Efficacy of Intratumoral Injection and Intrasplenic Injection with a Mutant HSV for the Treatment of Liver Metastasis of Colon Cancer," (No. 4383) Immunology/Experimental and Preclinical 12: Vaccines and Tumor Antigens II Experimental/Molecular Therapeutics Mar. 2001 vol. 42.

(Continued)

*Primary Examiner*—Bruce R. Campell
*Assistant Examiner*—Bao Qun Li
(74) *Attorney, Agent, or Firm*—Barnes & Thornburg LLP

(57) ABSTRACT

It is intended to provide highly safe antitumor agents which exhibit an antitumor effect on human remote tumors such as metastatic tumors too and by which an antitumor immune reaction enabling an immune therapy for cancer can be induced, tumor immunity inducers, T cell activators, dendritic cell activators, a method of treating cancer using the same, etc. Inactivated herpes simplex virus (inactivated HSV), herpes simplex virus glycoprotein D (HSVgD), etc. are employed as the active ingredients of antitumor agents, tumor immunity inducers, T cell activators or dendritic cell activators. As a specific example of the treatment for the above-described inactivation, citation may be made of a combination of UV-irradiation using ultraviolet light at 254 nm at 4 $J/m^2$ for 30 minutes with heating at 56° C. for 30 minutes.

4 Claims, 9 Drawing Sheets

OTHER PUBLICATIONS

Endo, Takashi et al., "Cancer Vaccination Therapy for the Liver Metastasis of Colon Cancer," Nihongangakkai Sokai Kiji, 2001, vol. 60, p. 621 (Japanese abstract No. 2182 only).

Fearon, Eric R. et al., "Induction in a Murine Tumor of Immunogenic Tumor Variants by Transfection with a Foreign Gene," Cancer Research, Jun. 1, 1988, vol. 48, pp. 2975-2980.

Ghiasi, Homayon et al., "Specific and Nonspecific Immune Stimulation of MHC-II Deficient Mice Results in Chronic HSV-1 Infection of the Trigeminal Ganglia Following Ocular Challenge," Virology, 1999, vol. 258, pp. 208-216.

Hitsumoto, Yasuo et al., "Preparation of Membrane Fraction from Herpes Simplex Virus-Infected Cells Which Induct Cytotoxic T Lymphocytes," Microbiol. Immunol., 1983, vol. 27 (9), pp. 757-765.

Huang, Alex Y. C. et al., "The immunodominant major histocompatibility complex class I-restricted antigen of a murine colon tumor derives from an endogenous retroviral gene product," Proc. Natl. Acad. Sci., USA, Sep. 1996, vol. 93, pp. 9730-9735.

Iizuka, Yukihiko et al., "A Simple and Effective Therapeutic Approach for the Induction of Antitumor Immunity with Replication-Conditional Mutant HSV," Immunology/Experimental and Preclinical 12, Proceedings of the American Association for Cancer Research, Mar. 2001, vol. 42, p. 817 (No. 4386).

Johnson, David C. et al., "Herpes Simplex Viruses Lacking Glycoprotein D Are Unable To Inhibit Virus Penetration: Quantitative evidence for Virus-Specific Cell Surface Receptors," Journal of Virology, Dec. 1988, pp. 4605-4612.

Markert, JM et al., "Conditionally replicating herpes simplex virus mutant, G207 for the treatment of malignant glioma: results of a phase I trial," Gene Therapy, 2000, vol. 7, pp. 867-874.

Mineta, Toshihiro et al., "Attenuated multi-mutated herpes simplex virus-1 for the treament of malignant gliomas," Nature Medicine, Sep. 1995, vol. 1, No. 9, pp. 938-943,.

Mueller, Daniel L. et al., "Clonal Expansion Versus Functional Clonal Inactivation: A Costimulatory Signalling Pathway Determines the Outcome of T Cell Antigen Receptor Occupancy," Am. Rev. Immunol. 1989, vol. 7, pp. 445-480.

Roth, Claude et al., "Immune Response Against Tumors," Advances in Immunology, vol. 57, p. 281-351.

Tabor, Edward et al., "Brief Communication: Inactivation of Hepatitis B Virus By Heat In Antithrombin III Stabilized With Citrate," Thrombosis Research, 1981, vol. 22: 233-238.

Tamada, Koji et al., "Modulation of T-cell mediated immunity in tumor and graft-versus-host disease models through the Light co-stimulatory pathway," Nature Medicine, Mar. 2000, vol. 6, No. 3, pp. 283-289.

Toda, Masahiro et al., "In Situ Cancer Vaccination: An IL-12 Defective Vector/Replication-Competent Herpes Simplex Virus Combination Induces Local and Systemic Antitumor Activity," The Journal of Immunology, 1998, vol. 160, pp. 4457-4464.

Toda, Masahiro Toda et al., "Treatment of Human Breast Cancer in a Brain Metastatic Model by G207 a Replication-Competent Multimutated Herpes Simplex Virus 1," Human Gene Therapy, Oct. 10, 1998, vol. 9, pp. 2177-2185 ( ).

Toda, Masahiro et al., "Herpes Simplex Virus as an in Situ Cancer Vaccine for the Induction of Specific Anti-Tumor Immunity," Human Gene Therapy, Feb. 10, 1999, vol. 10, pp. 385-393.

Wentz, W. Budd et al., "Effect of Prior Immunization on Induction of Cervical Cancer in Mice by Herpes Simplex Virus Type 2," Science, vol. 222, pp. 222-223.

Yazaki, Takahito et al., "Treatment of Human Malignant Meningiomas by G207, a Replication-competent Multimutated Herpes Simplex Virus 1," Cancer Research, Nov. 1, 1995, vol. 55, pp. 4752-4756.

Yoon, San S. et al., "An oncolytic herpes simplex virus type 1 selectively destroys diffuse liver metastases from colon carcinoma," The FASEB Journal, Feb. 2000, vol. 14, pp. 301-311.

Yuasa, T. et al., "Overproduction of gamma interferon in B/Jas inbred rabbits with herpes simplex virus encephalitis," Microbiol. Immunol. 1999, vol. 43(4), pp. 365-371.

Jennings, R., et al., "Herpesvirus Vaccines. An Update", *BioDrugs*, vol. 10, No. 4, pp. 257-264, (1998).

Boursnell, M.E.G., et al., "Disabled Infectious Single Cycle (Disc) Herpes Simplex Virus As A Vector For Immunotherapy of Cancer", *Adv. Exp. Med. Biol.*, vol. 451, pp. 379-384, (1998).

Kimura, Hiroshi, "Prophylaxis and treatment of α herpesvirus infection—vaccine", vol. 58, No. 4, pp. 928-932, (2000).

Flo, J., et al., "Modulation of the immune response to DNA vaccine by co-delivery of costimulatory molecules", *Immunology*, vol. 100, No. 2, pp. 259-267, (2000).

Lee, J. Y., et al., "Analysis of the antitumor effect of different Her-2/ncu-expressing plasmid DNAs in a syngeneic tumor model", *FASEB Journal*, vol. 16, No. 4, p. A333, 246.5, (Mar. 20, 2002).

Terhune, S.S., et al., "Limited Variability of Glycoprotein Gene Sequences and Neutralizing Targets in Herpes Simplex Virus Type 2 Isolates and Stability on Passage in Cell Culture", *J. Infect. Dis.*, vol. 178, No. 1, pp. 8-15, (1998).

Kawakami, Yutaka, "Gene therapy of cancer", vol. 29, No. 3, pp. 194-202, (1994) Translation pp-1020).

Mikloska, Z. et al., "Herpes simplex virus type 1 glycoproteins gB, gC and gD are major targets for CD4 T-lymphocyte cytotoxicity in HLA-DR expressing human epidermal keratinocytes," Journal of General Virology, vol. 79, (1998), pp. 353-361.

* cited by examiner

_US 7,384,627 B2_

ANTITUMOR AGENTS WITH THE USE OF HSV

CROSS-REFERENCE TO RELATED APPLICATIONS

This application is a U.S. national counterpart application of international application Ser. No. PCT/JP03/05626 filed May 2, 2003, which claims priority to Japanese applications serial nos. 2002-130954, 2002-206291, and 2002-319157 filed May 2, 2002; Jul. 15, 2002; and Oct. 31, 2002, respectively.

TECHNICAL FIELD

The present invention relates to antitumor agents, tumor immunity inducers, T cell activators, and dendritic cell activators that exhibit antitumor effects on human distant tumors such as metastatic tumors as well, and that contain an inactivated herpes simplex virus (inactivated HSV) or herpes simplex virus glycoprotein D (HSVgD) etc. as an effective ingredient. The present invention also relates to enhancement of antitumor effects, methods for treating distant tumors such as metastatic tumors, methods for inducing tumor immunity, methods for identifying tumor antigens, methods for activating T cells, and methods for activating dendritic cells based on the use of the above-mentioned agents, inducers, or activators.

BACKGROUND ART

Induction of tumor-specific immunity enables long-term prevention of recurrence of tumors. Such immunotherapy, however, basically depends on the presence or absence of tumor specific antigens and on whether or not a cytotoxic immune response can be induced, in which an antigen is presented and tumor cells are recognized. Cytotoxic T lymphocytes (CTLs), together with costimulatory molecules, recognize MHC class I molecules complexed with peptides derived from cytoplasmic proteins presented on the cell surface (refer to e.g., non-patent literature 1). Tumor-specific antigens have been detected in various human tumors (refer to e.g., non-patent literatures 2 and 3). Cancer vaccine therapy has focused either on the use of inactivated tumor cells or their lysates administered together with an adjuvant or a cytokine. It was recently reported that gene transfer of various cytokines, MHC molecules, costimulatory molecules, or tumor antigens to tumor cells enhances the visibility of tumor cells to immune effector cells (refer to e.g., non-patent literature 4). If induction of antitumor immunity becomes possible by direct intratumoral inoculation (in situ cancer vaccine) of HSV etc, major problems in using cancer vaccines for therapeutic purposes will be overcome. That is, the harvest of patients' autologous tumor cells, their in vitro manipulation such as culture and irradiation and identification of specific tumor antigens will not be needed for preparation of cancer vaccines.

HSV is a double-stranded DNA virus, contains the largest genome (153 kb) among DNA viruses that proliferate in nuclei, which encodes 84 kinds of open reading frames. The genome consists of the L (long) and S (short) components, each having a unique sequence flanked by inverted repeat sequences on its both sides. The complete nucleotide sequence of the viral genome has been determined and the functions of almost all viral genes have been elucidated. Martuza et al. developed herpes simplex virus mutant G207, a multi-gene mutant of herpes simplex virus type 1 (HSV-1) with a deletion in the $\gamma34.5$ gene and a lacZ gene insertion in the ICP6 gene (refer to e.g., non-patent literature 5). G207 is superior to other virus vectors from the therapeutic viewpoint. G207 is replicated in dividing cells, thereby causing lysis and death of infected cells, whereas in non-dividing cells, the virus proliferation is markedly weak. Inoculation with G207 into tumors established in athymia mice suppressed the tumor growth due to tumor-specific replication and prolonged the survival period of tumor-bearing mice (refer to e.g., non-patent literature 6). Further, in immune responsive mice, intratumoral inoculation with G207 induces tumor-specific immune responses, thereby suppressing the growth of tumors that have not been inoculated with G207 as well (refer to e.g., non-patent literature 7). In this case, G207 is acting as an in situ cancer vaccine (refer to e.g., patent literature 1). To date, gene therapy using herpes simplex virus mutant G207 has been performed, focusing on brain tumors, and their clinical application has also started in the U.S. (refer to e.g., non-patent literature 8).

The murine colon carcinoma cell line CT26 is poorly immunogenic and does not induce tumor-specific CTLs at the detectable level. CT26 is widely used as a syngeneic tumor model to study immunotherapy (refer to e.g., non-patent literatures 9 and 10). As a tumor-specific antigen in CT26, the MHC class I-restricted AH1 peptide, derived from an envelop protein (gp70) of an endogenous murine leukemia virus, was identified (refer to e.g., non-patent literature 10). It was confirmed that CT26 tumors which have been subcutaneously established can be treated by adoptive immunity cell transfer of peptide-specific CTLs and that there is a correlation between induction of tumor-specific CTLs and antitumor effects (refer to e.g., non-patent literature 10). To investigate the efficacy of HSV-1 mutant G207 as an in situ cancer vaccine, the inventors have used the poorly-immunogenic murine colon carcinoma cell line CT26, which expresses the tumor antigen identified. Further, the inventors have evaluated the efficacy of G207 using the syngeneic M3 mouse melanoma model to clarify that antitumor responses induced by intratumoral inoculation with G207 can be commonly used (refer to e.g., non-patent literatures 11 and 12).

On the other hand, following methods for inactivating viruses are known: (a) physical inactivation methods such as heat treatment (refer to e.g., non-patent literature 13), ultra-violet irradiation (refer to e.g., patent literature 2), γ-irradiation (refer to e.g., patent literature 3), electron beam irradiation (refer to e.g., patent literatures 4 and 5), pressure treatment (refer to e.g., patent literature 6), and energizing treatment (refer to e.g., patent literature 7); (b) chemical inactivation methods such as sterilization using phenol, formalin, alcohol, etc., alkaline treatment (refer to e.g., patent literature 8), contact with singlet oxygen, which consists of normal oxygen molecules excited electronically and being at the high state in energy (refer to e.g., patent literature 9), and deoxyribonuclease treatment; and (c) the combination of these physical inactivation methods and chemical inactivation methods (refer to e.g., patent literatures 10 and 11).

In addition, the following are described regarding HSVgD as vaccines against herpes viruses: methods of producing recombinant HSVgD (refer to e.g., patent literature 12), recombinant HSVgD vaccine (refer to e.g., patent literature 13), recombinant DNA encoding HSV-2gD and the protein (refer to e.g., patent literature 14), vaccine formulations consisting of HSVgD and 3-deacylated monophosphoryl lipid A (refer to e.g., patent literature 15), methods of producing recombinant HSVgD using insect cells (refer to e.g., patent literature 16), the HSVgD molecule consisting of 300 amino acid sequences (refer to e.g., patent literature 17), a vaccine composition containing HSVgD or an HBV antigen in conjunction with an adjuvant (refer to e.g., patent literature 18), and a fusion protein of HSVgB polypeptide and HSVgD (refer to e.g., patent literature 19). However, nothing has been known of using HSVgD for a cancer vaccine.

Patent literature 1: National Publication of International Patent Application No. 2001-513508
Patent literature 2: Japanese Patent Publication No. 45-9556
Patent literature 3: Japanese Laid-Open Application No. 2-9367
Patent literature 4: Japanese Laid-Open Application No. 4-200353
Patent literature 5: Japanese Laid-Open Application No. 4-92671
Patent literature 6: Japanese Laid-Open Application No. 6-142197
Patent literature 7: Japanese Laid-Open Application No. 2000-175682
Patent literature 8: Japanese Laid-Open Application No. 9-187273
Patent literature 9: Japanese Laid-Open Application No. 11-199490
Patent literature 10: Japanese Laid-Open Application No. 6-321994
Patent literature 11: National Publication of International Patent Application No. 8-504407
Patent literature 12: EP101655
Patent literature 13: EP-A-628633
Patent literature 14: WO90/13652
Patent literature 15: U.S. Pat. No. 6,027,730
Patent literature 16: EP-A-531728
Patent literature 17: U.S. Pat. No. 5,654,174
Patent literature 18: National Publication of International Patent Application No. 2002-506045
Patent literature 19: Japanese Patent No. 2999966
Non-patent literature 1: Annu. Rev. Immunol. 7, 445-480, 1989
Non-patent literature 2: Annu. Rev. Immunol. 12, 337-365, 1994
Non-patent literature 3: Adv. Immunol. 57, 281-351, 1994
Non-patent literature 4: Adv. Immunol. 58, 417-454, 1995
Non-patent literature 5: Nat. Med. 1, 938, 1995
Non-patent literature 6: Cancer. Res. 55, 4752, 1995
Non-patent literature 7: Hum. Gene Ther. 9, 2177-2185, 1999
Non-patent literature 8: Gene Ther, 7, 867-874, 2000
Non-patent literature 9: Cancer Res. 35, 2975, 1988
Non-patent literature 10: Proc. Natl. Acad. Sci. USA 93, 9730, 1996,
Non-patent literature 11: Hum. Gene Ther. 10, 385-393, 1999
Non-patent literature 12: J. Immunol. 160, 4457-4464, 1998
Non-patent literature 13: Thrombosis Research, 22, 233-238, 1981

Metastasis of cancer is a pathologic condition that is extremely difficult to treat; there have been no effective treatment to date. Although it has been reported that some limited number of chemotherapeutic drugs are efficacious, their side effects are regarded as questionable. In spite of recent drastic advancements in gene therapy using virus vectors, there are serious problems in terms of safety. An object of the present invention is to provide an antitumor agent, a tumor immunity inducer, a T cell activator, and a dendritic cell activator, which are extremely safe and capable of inducing an antitumor immune reaction enabling immunotherapy for a cancer in such a way that an antitumor effect on a human distant tumor such as a metastatic tumor is exhibited. Another object of the present invention is to provide, using such an agent, inducer, or activator, enhancement of an antitumor effect, a method for treating a distant tumor such as a metastatic tumor, a method for inducing tumor immunity, a method for identifying a tumor antigen, a method for activating T cells, and a method for activating dendritic cells.

The inventors have enthusiastically studied to solve the above-mentioned problems. Considering, in putting cancer therapy by virus vectors into practical use, safety in their use is a prerequisite, they prepared the inactivated HSV that was completely devoid of infectivity and has virus DNA destroyed, by subjecting the wild-type HSV to ultraviolet irradiation and heat treatment. They inoculated this inactivated HSV directly into malignant tumor tissues derived from the tumor cell line CT26 and found that a tumor-specific immune response was induced and malignant tumors have regressed. They also found that the inactivated HSV was able to similarly suppress the growth of distant malignant tumors that have not been directly inoculated and that the inactivated HSV activated human dendritic cells. Likewise, they inoculated HSVgD directly into malignant tumor tissues derived from the tumor cell line CT2 and found that a tumor specific immune response was induced and malignant tumors regressed and that the growth of distant malignant tumors that have not been directly inoculated was suppressed. They also found that HSVgD worked to activate T cells as a costimulatory factor for T cells and activated human dendritic cells. The present invention has been accomplished based on these findings.

DISCLOSURE OF INVENTION

Thus, the present invention relates to the following: An antitumor agent comprising as an effective ingredient an inactivated herpes simplex virus or a herpes simplex virus glycoprotein (claim 1); the antitumor agent of claim 1, containing as a main ingredient the herpes simplex virus that has been inactivated by an ultraviolet treatment and a heat treatment (claim 2); the antitumor agent of claim 1, in which the ultraviolet treatment is an irradiation at 4 $J/m^2$ for 30 min using a 254 nm ultraviolet light (claim 3); the antitumor agent of claim 2, in which the heat treatment is a heating at 56° C. for 30 min (claim 4); the antitumor agent of claim 1, in which the herpes simplex virus glycoprotein is herpes simplex virus glycoprotein D (claim 5); the antitumor agent of any one of claims 1 to 5, in which the herpes simplex virus is the KOS strain of herpes simplex virus type 1 or the 169 strain of herpes simplex virus type 2 (claim 6); a method for treating a tumor, containing administering the antitumor agent of any one of claims 1 to 5 directly to the tumor tissue (claim 7); a method for treating a distant tumor, such as a metastatic tumor, containing administering the antitumor agent of any one of claims 1 to 5 directly to the tumor tissue (claim 8); a tumor immunity inducer containing as an effective ingredient an inactivated herpes simplex virus or a herpes simplex virus glycoprotein (claim 9); the tumor immunity inducer of claim 9, containing as a main ingredient the herpes simplex virus inactivated by an ultraviolet treatment and a heat treatment (claim 10); the tumor immunity inducer of claim 10, in which the ultraviolet treatment is an irradiation at 4 $J/m^2$ for 30 min using a 254 nm ultraviolet light (claim 11); the tumor immunity inducer of claim 10, in which the heat treatment is a heating at 56° C.

for 30 min (claim 12); the tumor immunity inducer of claim 9, in which the herpes simplex virus glycoprotein is herpes simplex virus glycoprotein D (claim 13); the tumor immunity inducer of any of one of claims 9 to 13, in which the herpes simplex virus is the KOS strain of herpes simplex virus type 1 or the 169 strain of herpes simplex virus type 2 (claim 14); a method for inducing tumor immunity, containing inducing a cytotoxic T lymphocytes (CTL) and/or an antibody reaction by administering the tumor immunity inducer of any one of claims 9 to 14 directly to the tumor tissue (claim 15); a method for identifying a tumor antigen, containing inducing a cytotoxic T lymphocytes (CTL) and/or an antibody reaction by administering the tumor immunity inducer of any one of claims 9 to 14 directly to the tumor tissue and using the induced cytotoxic T lymphocyte (CTLs) and/or antibody (claim 16); a T cell activator containing as effective ingredient a inactivated herpes simplex virus or a herpes simplex virus glycoprotein (claim 17); the T cell activator of claim 17, containing as a main ingredient the herpes simplex virus inactivated by an ultraviolet treatment and a heat treatment (claim 18); the T cell activator of claim 18, in which the ultraviolet treatment is an irradiation at 4 J/m$^2$ for 30 min using a 254 nm ultraviolet light (claim 19); the T cell activator of claim 18, in which the heat treatment is a heating at 56° C. for 30 min (claim 20); the T cell activator of claim 17, in which the herpes simplex virus glycoprotein is herpes simplex virus glycoprotein D (claim 21); the T cell activator of any one of claims 17 to 21, in which the herpes simplex virus is the KOS strain of herpes simplex virus type 1 or the 169 strain of herpes simplex virus type 2 (claim 22); a method for activating a T cell, in which the T cell activator of any one of claims 17 to 22 is used (claim 23); a dendritic cell activator, containing as an effective ingredient a inactivated herpes simplex virus or a herpes simplex virus glycoprotein (claim 24); the dendritic cell activator of claim 24, containing as a main ingredient the herpes simplex virus inactivated by an ultraviolet treatment and a heat treatment (claim 25); the dendritic cell activator of claim 25, in which the ultraviolet treatment is an irradiation at 4 J/m$^2$ for 30 min using a 254 nm ultraviolet light (claim 26); the dendritic cell activator of claim 25, in which the heat treatment is a heating at 56° C. for 30 min (claim 27); the dendritic cell activator of claim 24, in which the herpes simplex virus glycoprotein is herpes simplex virus glycoprotein D (claim 28); the dendritic cell activator of any one of claims 24 to 28, in which the herpes simplex virus is the KOS strain of herpes simplex virus type 1 or the 169 strain of herpes simplex virus type 2 (claim 29); and a method for activating a dendritic cell containing administrating the tumor cell activator of any one of claims 24 to 29 directly to the tumor tissue (claim 30).

BEST MODE FOR CARRYING OUT THE INVENTION

Figure 1:
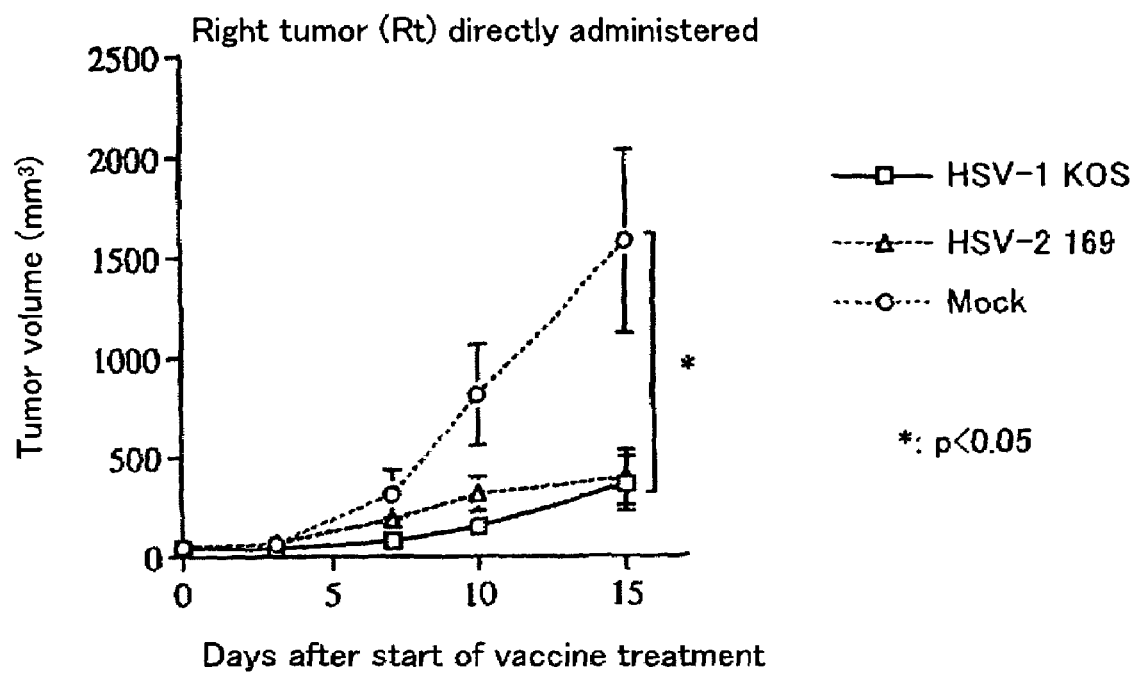
FIG. 1 shows that, compared with the mock-inoculated control group, the intratumoral inoculation with inactivated HSV-1 KOS or inactivated HSV-2 169 suppress the growth of the inoculated tumor (right tumor: Rt). (Vertical axis: tumor volume, horizontal axis: days after the start of vaccine treatment)

The antitumor agents, tumor immunity inducers, T cell activators, and dendritic cell activators according to the present invention are not particularly limited, as long as they contain as an effective ingredient an inactivated HSV, or an HSV glycoprotein such as herpes simplex virus glycoproteins D (HSVgD), B (HSVgB), or C (HSVgC). The above-mentioned antitumor agents and tumor immunity inducers are extremely useful as in situ cancer vaccines. It is extremely preferable that "in situ" herein means direct inoculation into malignant tumor tissue. The above-mentioned inactivation methods can be known virus inactivation methods including physical inactivation methods such as heat treatment, ultraviolet irradiation, gamma irradiation, electron beam irradiation, pressure treatment, energizing treatment; chemical inactivation methods such as sterilization using phenol, formalin, and alcohol, alkaline treatment, and deoxyribonuclease treatment; and methods combining these physical inactivation methods with chemical inactivation methods such as heat treatment in the presence of detergent. Mutagenesis by gene manipulation, however, is not included in inactivation methods herein.

Among these virus inactivation methods, the inactivation method combining the treatment of destroying virus DNA (e.g., ultraviolet treatment) with protein denaturation treatment (e.g., heat treatment) that eliminates infectivity is particularly preferable in terms of safety of cancer vaccines. Preferably as such UV treatment, an irradiation at 1-10 J/m$^2$, particularly at 4 J/m$^2$ for 5-60 min, more particularly for 30 min, using far-ultraviolet light at a wavelength of 190-300 nm having the effect of inducing injury of genes in an organism, particularly ultraviolet light of 254 nm, which is absorbed by DNA and RNA bases and stops replication in cell division by dimers, such as thymine-thymine, thymine-cytosine, cytosine-cytosine, and uracil-uracil, formed by the absorbed light quantum energy, is illustrated. Preferably as heat treatment, heating at 45-80° C. for 5-10 hours, preferably at 56° C. for 30 minutes is illustrated.

Herpes simplex viruses to be inactivated in the production of the antitumor agents, tumor immunity inducers, T cell activators, or dendritic cell activators according to the present invention include HSV-1 and herpes simplex virus type 2 (HSV-2) wild strains as well as mutant strains mutagenized by gene manipulation. They are preferably completely free of anything harmful after inactivation treatment. One specific preferable example is the wild-type HSV, such as, for example, the KOS strain of HSV-1 or the 169 strain of HSV-2. Further, aforementioned HSV glycoproteins such as HSVgD, HSVgB, and HSVgC include HSV glycoproteins such as gD (glycoprotein D), gB (glycoprotein B), gC (glycoprotein C), etc. derived from mutant strains mutagenized by gene manipulation and inactivated strains, in addition to HSV-1 and HSV-2 wild-type strains. These HSV glycoproteins can preferably be produced as recombinant proteins, using bacteria (e.g., *E. coli*), yeasts, insect cells, mammalian cells, etc. as host cells.

The antitumor agents and tumor immunity inducers according to the present invention are useful as a preventive drug or a therapeutic agent for recurrence and metastasis of cancers such as malignant brain tumor, serving as an in situ cancer vaccine. T cell activators and dendritic cell activators according to the present invention are useful as a preventive drug and a therapeutic agent for recurrence and metastasis of cancers such as malignant brain tumors as well as for various other diseases that require activation of T cells and that of dendritic cells (enhancement of antigen-presenting capability etc.). When such agents, inducers, or activators are used as pharmaceuticals, various mixing ingredients for preparation, such as a pharmaceutically acceptable common carrier, a binder, a stabilizer, an excipient, a diluent, a buffer, a disintegrator, a solubilizer, a solubilizing agent, and a tension agent can be added. Such preventative or therapeutic agents can be administered orally or parenterally. That is, they may be administered orally in commonly used administration forms such as, for example, powders, granules, capsules, syrups, and suspensions, or parenterally in the form of an injection in dose forms such as a solution, an emulsion, and a suspension. The agents may also be administered in a spray form into the nostrils. However, it is preferable to inoculate them directly to malignant tumor tissue in that immediate tumor specific immune responses can be induced.

The methods for treating tumors according to the present invention, preferably the ones for treating distant tumors such as metastatic tumors are not particularly limited, as long as they are the treatment method in which an antitumor agent according to the present invention is administered by direct inoculation to a tumor tissue. Such therapeutic methods enable treatment and prevention of recurrence and metastatic of malignant tumors. The methods for inducing immune responses according to the present invention are not particularly limited as long as they are the method for inducing CTLs and/or an antibody reaction by administering the tumor immunity inducer according to the present invention directly to a tumor tissue. The use of the methods for inducing tumor immunity according to the present invention make it possible to investigate the mechanism of action of immune response induction, especially to a distant tumor by direct inoculation to a mouse and other tumor model. In addition, induction of CTLs and an antibody reactions to the living body is also possible. The methods for identifying tumor antigens according to the present invention are not particularly limited, as long as they are the method for inducing CTLs and/or an antibody reaction inside the living body by administering/inoculating a tumor immunity inducer according to the present invention directly to/into a mouse or other animal tumor model, and using the induced CTLs and/or the induced antibody. For example, identification of a new tumor antigen is enabled by performing gene transfer of a cDNA library into cells, co-culturing of mammalian cells that have expressed proteins encoded by the cDNAs together with CTLs induced, and analyzing the cDNA encoding the protein that the peptide recognized by the CTLs is originated.

The methods for activating T cells according to the present invention are not particularly limited, as long as they are the method for activating human or other animal T cells in vivo, in vitro, or ex vivo, using a T cell activator according to the present invention. However, in activating T cells in vivo, it is preferable to administer the T cell activator of the present invention directly to a tumor tissue. The methods for activating dendritic cells according to the present invention are not particularly limited, as long as they are the method for activating human or other mammalian dendritic cells in vivo, in vitro, or ex vivo, using a dendritic cell activator according to the present invention. However, in activating dendritic cells in vivo, it is preferable to administer the dendritic cell activator of the present invention directly to a tumor tissue. The use of the method for activating T cells and the method for activating dendritic cells according to the present invention enables treatment and research of diseases requiring activation of T cells and/or dendritic cells.

The present invention is explained with the following examples in more detail, but the technical scope of the present invention is not limited by these examples.

EXAMPLE 1

Viruses, Cell Lines, and Proliferation

As viruses, the KOS strain of HSV-1 and the 169 strain of HSV-2 (provided by Dr. Yoshiko Seto) were used. African green monkey kidney Vero cells (purchased from ATCC) were used for proliferation of HSVs. Vero cells were cultured in Dulbecco's modified Eagle's medium (DMEM) supplemented with 10% heat-inactivated fetal calf serum (IFCS), and in DMEM supplemented with 1% IFCS when viruses were proliferating. After repeating freeze-thaw of the cells in the virus buffer (150 mM NaCl-20 mM Tris pH7.5) and ultrasonicating the extract, viruses were recovered from the supernatant.

EXAMPLE 2

Inactivation of HSV

Test HSVs were subjected to inactivation treatment by ultraviolet treatment and heat treatment. The infection efficiency of the HSVs used before inactivation was $2 \times 10^8$ plaque-formation units/ml. As inactivation by ultraviolet rays, the viruses were irradiated at 4 J/m$^2$ for 30 min using 254 nm ultraviolet light on ice, according to the partly modified method of David C. J. et al. (J. virology, 62, 4605-4612, 1988). Subsequently, the UV-treated HSVs were subjected to heat treatment. As inactivation by heat treatment, thermal denaturation treatment of the HSVs were performed at 56° C. for 30 min according to the partly modified method of Hitsumoto Y et al. (Microbiol. Immunol., 27, 757-765, 1983).

EXAMPLE 3

Figure 2:
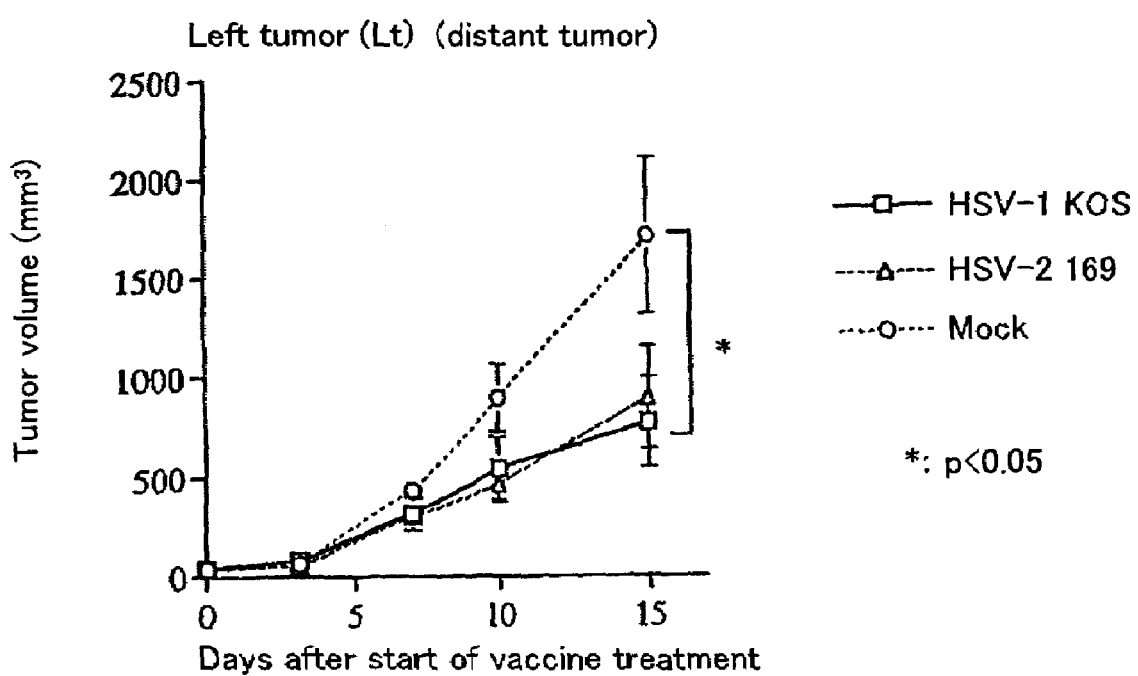
FIG. 2 shows that, compared with the mock-inoculated control group, the intratumoral inoculation with inactivated HSV-1 KOS or inactivated HSV-2 169 suppresses the growth of a distant tumor (right tumor: Rt). (Vertical axis: tumor volume, horizontal axis: days after the start of vaccine treatment)

In Situ Cancer Vaccine in a Mouse Bilateral Subcutaneous Tumor Model Using Inactivated HSV Six to eight-week old female BALB/c mice were anesthetized (with 0.25 ml of anesthetic liquid: 84% saline, 10% pentobarbital [50 mg/ml], 6% ethanol), and then $5\times10^5$ CT26 cells /100 µl was subcutaneously implanted bilaterally into mice. Treatment started when the diameter of the tumor reached about 5 mm. The extract of Vero cells used for virus preparation was UV-irradiated and heat-treated, and used as a control (hereinafter called "mock"). Either inactivated HSV or mock was administered only to the right tumor on days 0 and 3 after the start of treatment. Thereafter, the volumes of both of the tumors were periodically measured. Volume was calculated as major axis×(minor axis)$^2$÷2. FIG. 1 shows the result of the periodical changes in tumor volume of the right tumor (Rt), into which CT 26 was directly administered (inoculated). FIG. 2 shows the result of the periodical changes in tumor volume of the left tumor (Lt), which was a distant tumor. As observed in FIG. 1, in the inactivated HSV-1 KOS group (n=7) or the inactivated HSV-2 169 group (n=7), the growth of CT26 tumor was statistically significantly suppressed 15 days after the start of administration as compared with the mock group (n=6). FIG. 2 shows a similar result on the left distant tumor, to which inactivated HSV had not directly been administered. In the inactivated HSV-1 KOS group or the inactivated HSV-2 169 group, the growth of CT26 tumor was statistically significantly suppressed 15 days after the start of administration as compared with the mock group. These results indicated that the in situ cancer vaccine according to the present invention exhibits the antitumor effects on distant tumors as well.

EXAMPLE 4

Cytotoxic T Cell Activity Test with Inactivated HSV

Figure 3:
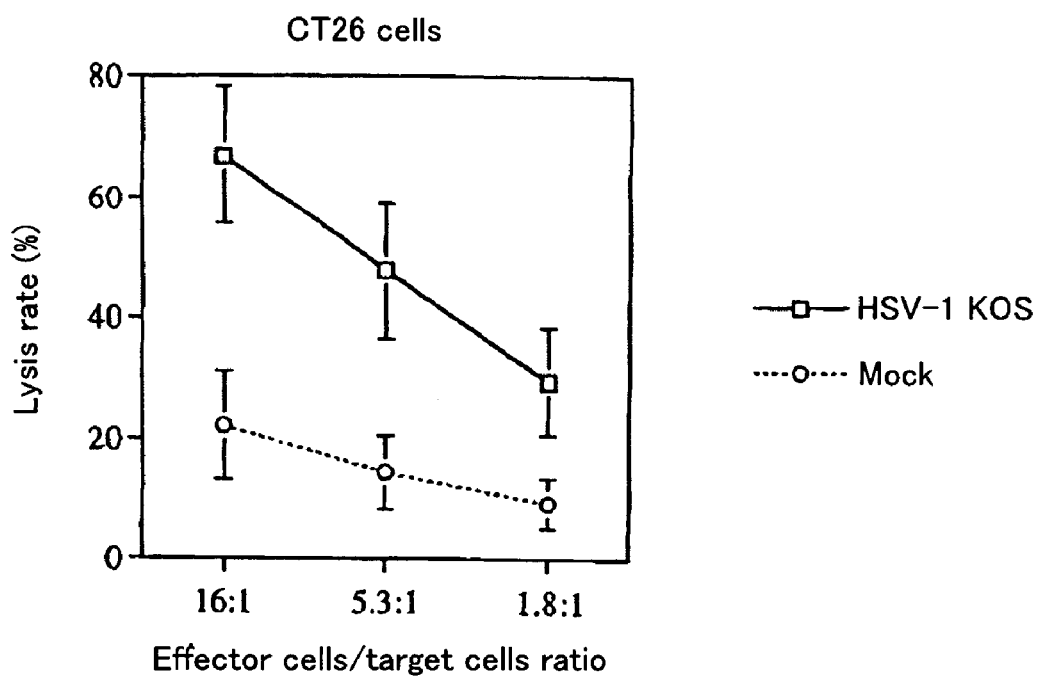
FIG. 3 shows cytotoxic T cell activity induced to CT26 cells by intratumoral inoculation of inactivated HSV-1 KOS.
Figure 4:
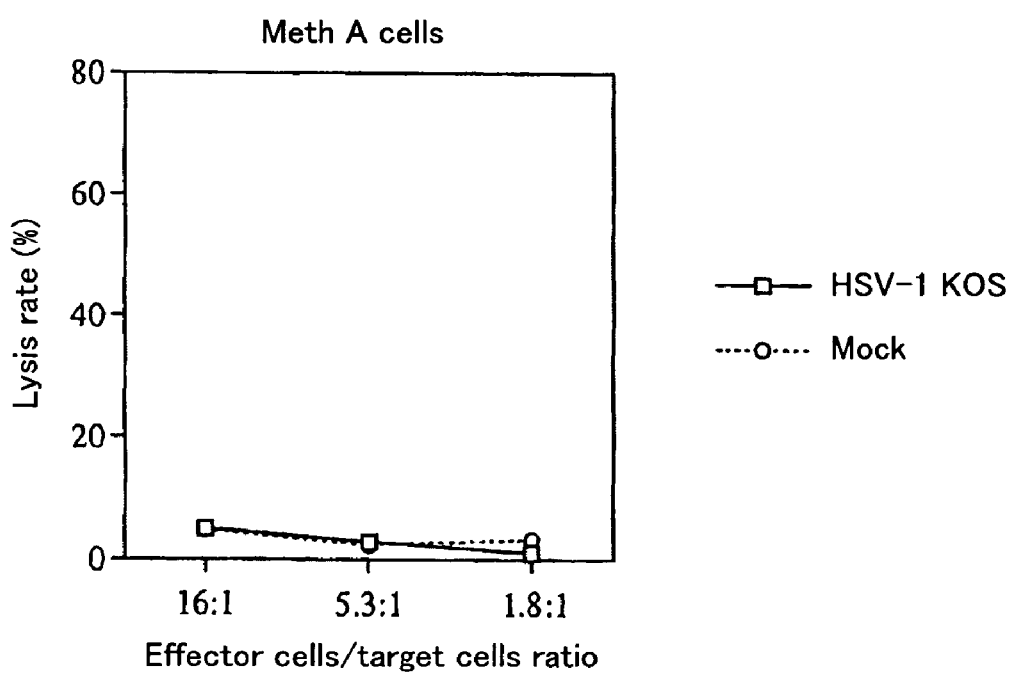
FIG. 4 shows cytotoxic T cell activity induced to Meth A cells by intratumoral inoculation of inactivated HSV-1 KOS.

Spleen cells were isolated from the mice that had received an in situ cancer vaccine (inactivated HSV-1 KOS strain) on day 10 after the start of treatment and were co-cultured with CT26 cells for seven days, and then $^{51}$Cr release test was performed. Either CT26 cells or Meth A cells into which 50 µCi of $^{51}$Cr had been incorporated were used as target cells. A total of $2.5\times10^3$ target cells, together with $4.0\times10^4$, $1.3\times10^4$, or $4.3\times10^3$ spleen cells as effector cells, were incubated at 37° C. for 4 hours in the presence of 5% carbon dioxide in a well of 96-well plates. $^{51}$Cr emitted into the culture supernatant was measured with a gamma counter. FIG. 3 and FIG. 4 show the result of the lysis rate of CT26 cells (n=3) Meth A cells (n=3), respectively, in various effector cell/target cell ratios (E/T ratios). As observed from FIG. 3, in the in situ cancer vaccine group, antitumor CTL activity was large compared with the mock group, and the larger the E/T ratio, the larger the difference of the antitumor CTL activity was. On the other hand, no CTL activity was induced in Meth A cells, either in the in situ cancer vaccine group or in the mock group. These results support the fact that the in situ cancer vaccine according to the present invention induces a specific tumor CTL activity.

EXAMPLE 5

Enhancement Effect of Antigen-Presenting Ability of Human Dendritic Cells by Inactivated HSV Immature dendritic cells were obtained from human peripheral blood by separating and culturing a CD14-positive subset by the immunomagnetic bead method. Specifically, a magnetic bead-coupled monoclonal antibody (20 µl/10$^7$ cells; manufactured by Miltenyi Biotec) against CD14 antigen was incubated with the cells at 4° C. for 15 min. The CD14-positive fraction was isolated by magnetically separating bead-bound cells using a magnetic cell separation system (MACS). The fraction was plated at a concentration of $1\times10^6$ cells/well and cultured for 6-7 days in RPMI medium containing 10% FBS (fetal bovine serum; Gb4) prepared to have 100 ng/ml of GM-CSF (manufactured by IBL Co., Ltd. ) and IL-4 (IBL) each. Immature dendritic cells were thus obtained. After confirming the expression of surface antigens (CD1a+, CD14−, CD80+, and CD86+) as immature dendritic cells with a flow cytometer, the inactivated HSV-1 KOS strain prepared by the method described in Example 2 was added to the medium at concentrations of multiplicity of infection (MOI)=0.1, 1, and 10 plaque-forming units (PUFs) /cells, which had been measured before inactivation, or alternatively mock was added instead of the virus, maturation factors TNF-α (manufactured by IBL Co., Ltd.) and IFN-γ (manufactured by IBL Co., Ltd.) were added 1 hour later at the final concentration of 10 ng/ml and 100 ng/ml, respectively, and the cells were incubated overnight. On the next day, the expression of the surface antigen CD83 (which was negative in immature dendritic cells) as mature dendritic cells was confirmed with a flow cytometer.

Figure 5:
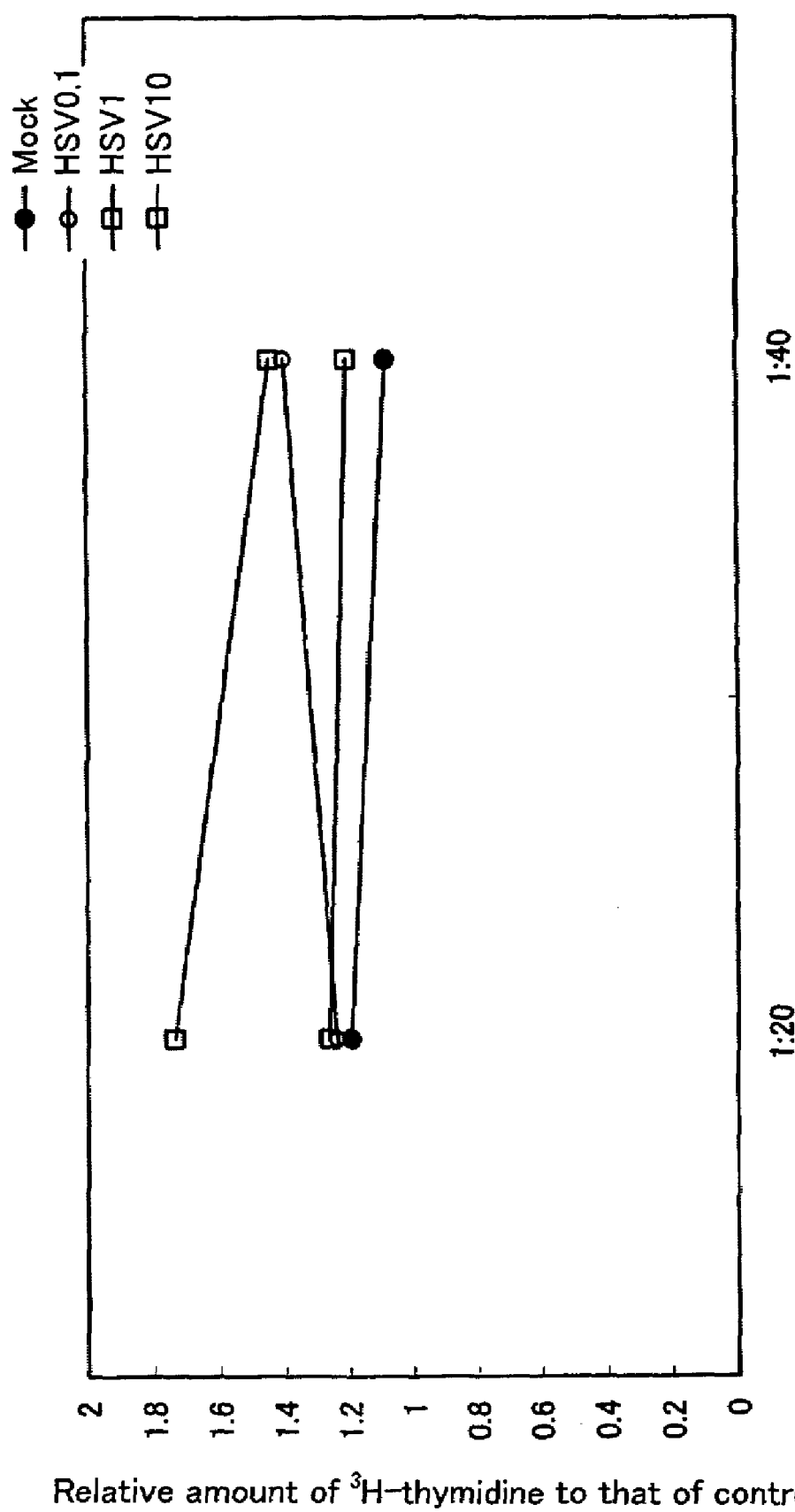
FIG. 5 shows effect of enhancing the antigen-presenting capability of human dendritic cells by inactivated HSV. In the FIG. 5, HSV0.1, HSV1 and HSV1O represent inactivation of HSV at MOI=0.1, 1, and 10, respectively, and DC: Responder represents the ratio of mature dendritic cells to allo-lymphocytes.

Subsequently, the mature dendritic cells induced with the addition of the inactivated HSV-1 KOS strain were examined for their ability to activate allo-lymphocytes. Mature dendritic cells induced by the addition of TNF-α (10 ng/ml) and IFN-γ (100 ng/ml) alone, without mock or inactivated HSV, were used as a control. The CD14-negative fraction of peripheral blood at a concentration of $6\times10^4$ cells as allo-lymphocytes (responders) and mature dendritic cells (DCs) as stimulators whose proliferation had been stopped by irradiation (15 Gy) were co-cultured (the ratio of DCs to responders was 1:20 or 1:40) for 3 days. The cultured lymphocytes were labeled with $^3$H thymidine at 0.027 Mbq/well for about 12 hours and the amount (CPM: counter per minute) of $^3$H-thymidine incorporated was measured using the top counter. FIG. 5 shows the relative amount of $^3$H-thymidine incorporated by lymphocytes after being co-cultured with mature dendritic cells to that of the control. As a result, it was indicated that mature dendritic cells to which the inactivated HSV-1 KOS strain was added have a higher ability to activate lymphocytes as compared with the control or inactivated mock. It was clarified by these results that the inactivated HSV has an effect of enhancing the antigen-presenting ability of human dendritic cells.

EXAMPLE 6

Figure 6:
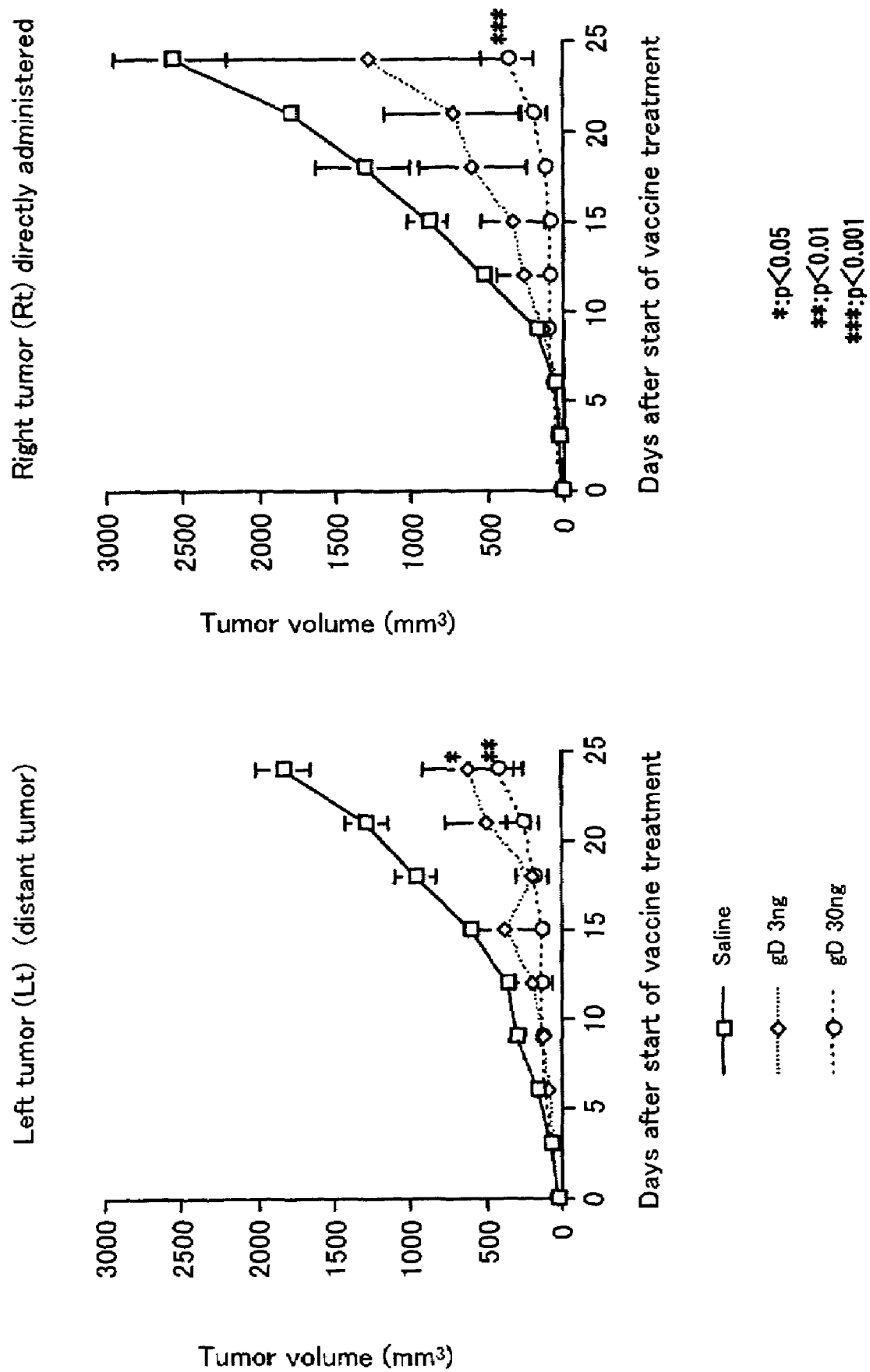
FIG. 6 shows that, compared with the saline-inoculated control group, the intratumoral inoculation with inactivated HSV-1gD suppresses the growth of the inoculated tumor (right tumor: Rt) as well as a distant tumor (left tumor: Lt).

In Situ Cancer Vaccine in a Mouse Bilateral Subcutaneous Tumor Model Using HSVgD Six to eight-week old female BALB/c mice were anesthetized (with 0.25 ml of anesthetic liquid: 84% saline, 10% pentobarbital [50 mg/ml], 6% ethanol), and then $5\times10^5$ cells/100 µl of CT26 was subcutaneously implanted bilaterally into mice. Treatment started when the diameter of the tumor reached about 5 mm. Saline was used as a control. Either saline solution of HSV type 1 (HSV-1) gD protein (manufactured by ViroStat Inc.) or saline was administered (30 μl each) only to the right tumor on days 0, 3, 6, and 9 after the start of treatment. Thereafter, the volumes of both of the tumors were periodically measured. Volume was calculated as major axis×(minor axis)$^2$÷2. FIG. 6 shows the result of the periodical changes in tumor volume of the right tumor (R) into which HSVgD was directly administered (inoculated), together with the result of the periodical changes in tumor volume of the left tumor (L) which was a distant tumor. As observed from FIG. 6 (right), in the HSVgD total dose (30 ng) group (n=7), the growth of CT26 tumors on the administered side was statistically significantly suppressed 24 days after the start of administration as compared with the saline solution group (n=3). FIG. 6 (left) indicated a similar result on the left distant tumor: In the HSVgD-13 ng group and the 30 ng group, the growth of CT26 tumors was statistically significantly suppressed 24 days after the start of administration as compared with the mock group. These results revealed that the in situ cancer vaccine according to the present invention exhibits an antitumor effect on distant tumors as well. Further, the HSVg antitumor effect was observed to depend on its dosage.

Figure 7:
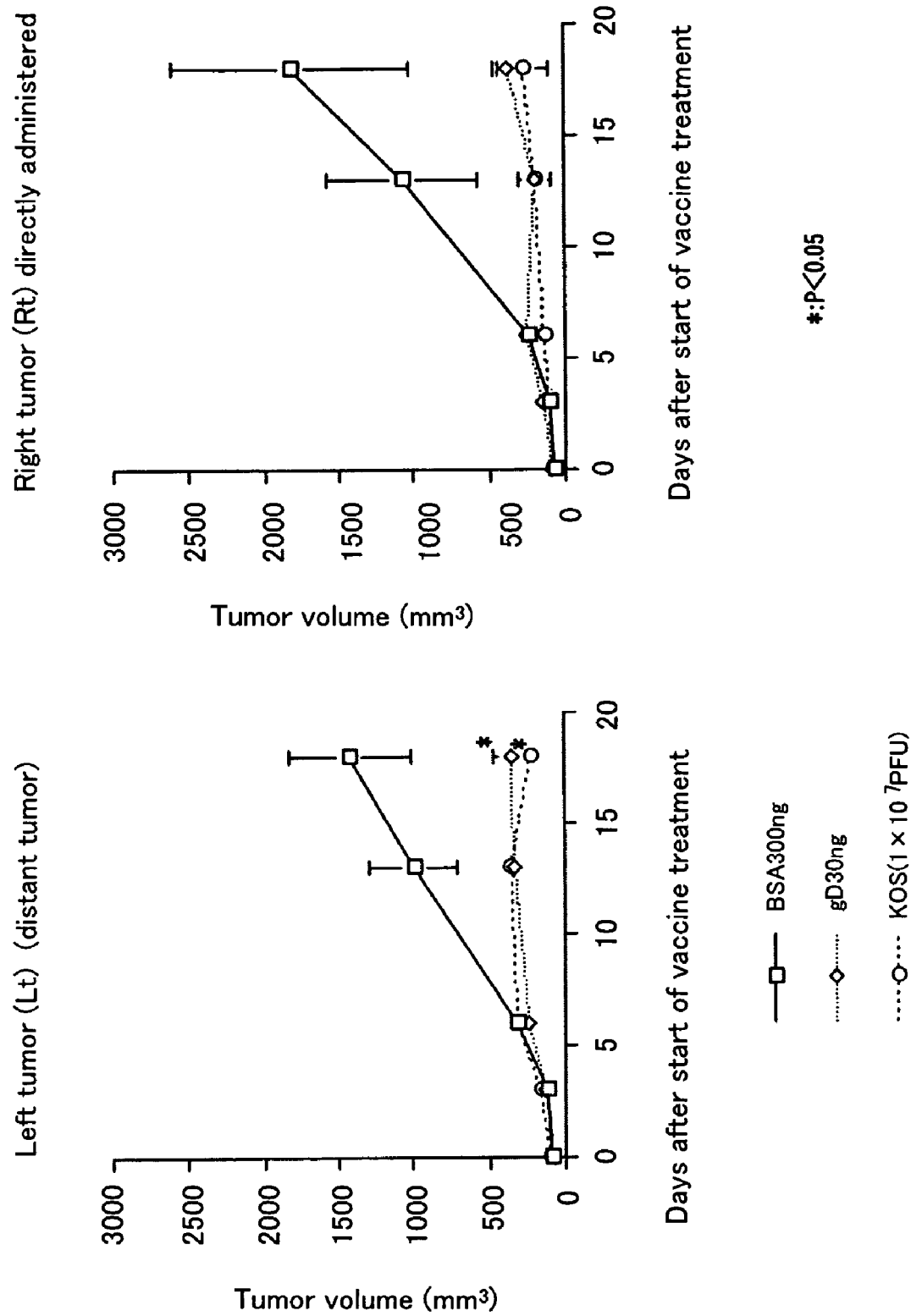
FIG. 7 shows that, compared with the saline-inoculated control group, the intratumoral inoculation with inactivated HSV-1gD suppresses the growth of the inoculated tumors (right tumor: Rt) as well as a distant tumor (left tumor: Lt) like intratumoral inoculation with inactivated HSV-1 KOS.

To reconfirm the antitumor effect of the in situ cancer vaccine using aforementioned HSVgD, BSA (manufactured by Sigma Chemical Corporation) was used as a negative control and inactivated HSV-1 KOS strain prepared in a similar manner to example 2 as a positive control. HSVgD or BSA dissolved in saline was administered (30 μl each) only to the right tumor on days 0, 3, and 6 after the start of the treatment. Thereafter, the volumes of both of the tumors were measured periodically. Inactivated HSV-1 KOS strain was administered (50 μl) only to the right tumor on day 0 and 3 after the start of the treatment. FIG. 7 shows a result of the periodical changes of the tumor volume of the right tumor (R), into which <HSVgD> was directly administered (inoculated), together with a result of the periodical changes of the tumor volume of the left tumor (L), which was a distant tumor. As observed from FIG. 7 (right), the HSVgD total dose (30 ng) (n=7) exhibited a behavior similar to that exhibited by the KOS group (the infection efficiency before inactivation: 2×107 PFU) (n=7). Eighteen days after the start of the administration, the growth of CT26 tumors on the administration side was suppressed as compared with the BSA total dose (300 ng) group (n=6). As observed from FIG. 7 (left), as for the left distant tumor to which HSVgD had not directly been administered, the HSVgD 30 ng group (n=8) exhibited a behavior similar to that exhibited by the KOS group (n=7). Eighteen days after the start of administration, the growth of CT26 tumors was statistically significantly suppressed as compared with the BSA total dose (300 ng) group (n=6). It was reconfirmed that the in situ cancer vaccine according to the present invention exhibits antitumor effects on distant tumors as well.

EXAMPLE 7

Effect of HSVgD on T Cells

Figure 8:
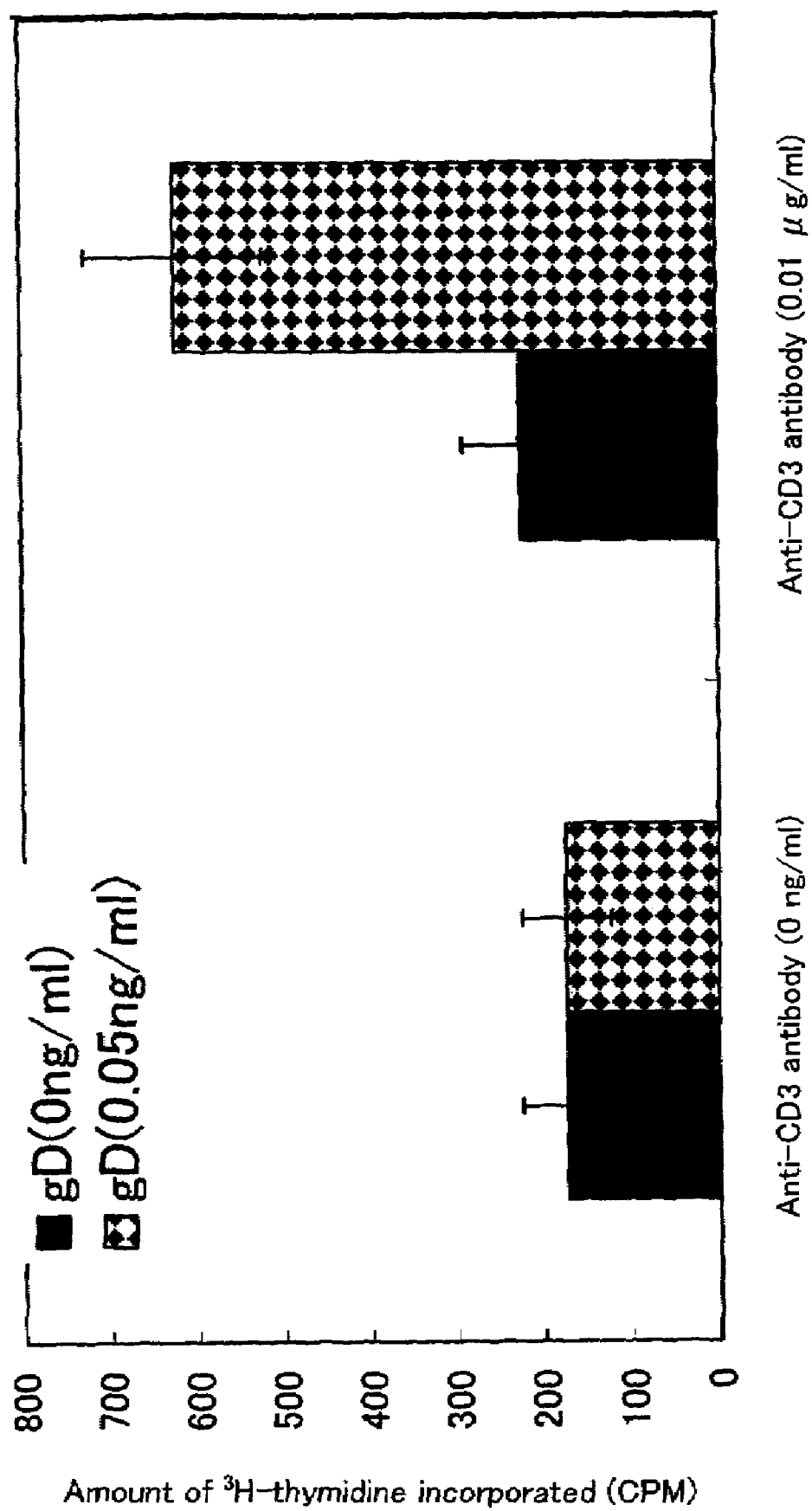
FIG. 8 shows T cell activation by costimulation of anti-CD3 antibody and HSV-1gD.

T cells were obtained from the lymph node of 6-week-old female C57BL/6 mice by the immunomagnetic bead method. Specifically, magnetic bead-coupled monoclonal antibodies (10 μl/10$^7$ cells each; manufactured by Miltenyi Biotec) against CD90, CD45R, MHC ClassII, and CD11c were incubated with the cells at 4° C. for 15 min. The T cell fraction was isolated by magnetically separating bead-bound cells using a magnetic cell separation system (MACS; manufactured by Miltenyi Biotec). The fraction (CD90+, CD45R−, MHC ClassII−, and CD11c−) was finally isolated as T cells. T cells (6×10$^4$ cells/well) were cultured for 5 days in the presence or absence of anti-CD3 antibody (0.01 ng/ml) and/or HSV-1 gD protein (0.05 ng/ml; manufactured by ViroStat Inc.). After labeling the cultured lymphocytes with $^3$H-thymidine for about 12 hours, the amount (CPM) of $^3$H-thymidine incorporated was measured by the top counter. The result is shown in FIG. 8. As observed from FIG. 8, it was revealed that T cells are not activated by either of the anti-CD3 antibody that stimulates the T cell receptor or HSV-1 gD that is a ligand for herpes-virus entry mediator (HVEM), but can be activated only when they are stimulated by both HSVgD and the anti-CD3 antibody. It has been found that LIGHT, a member of TNF cytokine family, activates T cells via HVEM as a costimulatory factor (Nat Med 6, 283-289, 2000). Being a ligand for HVEM, HSVgD has been revealed to work for activation of T cells by acting as a costimulatory factor to T cells.

EXAMPLE 8

Activation of T Cells by HSVgD Via HVEM

Figure 9:
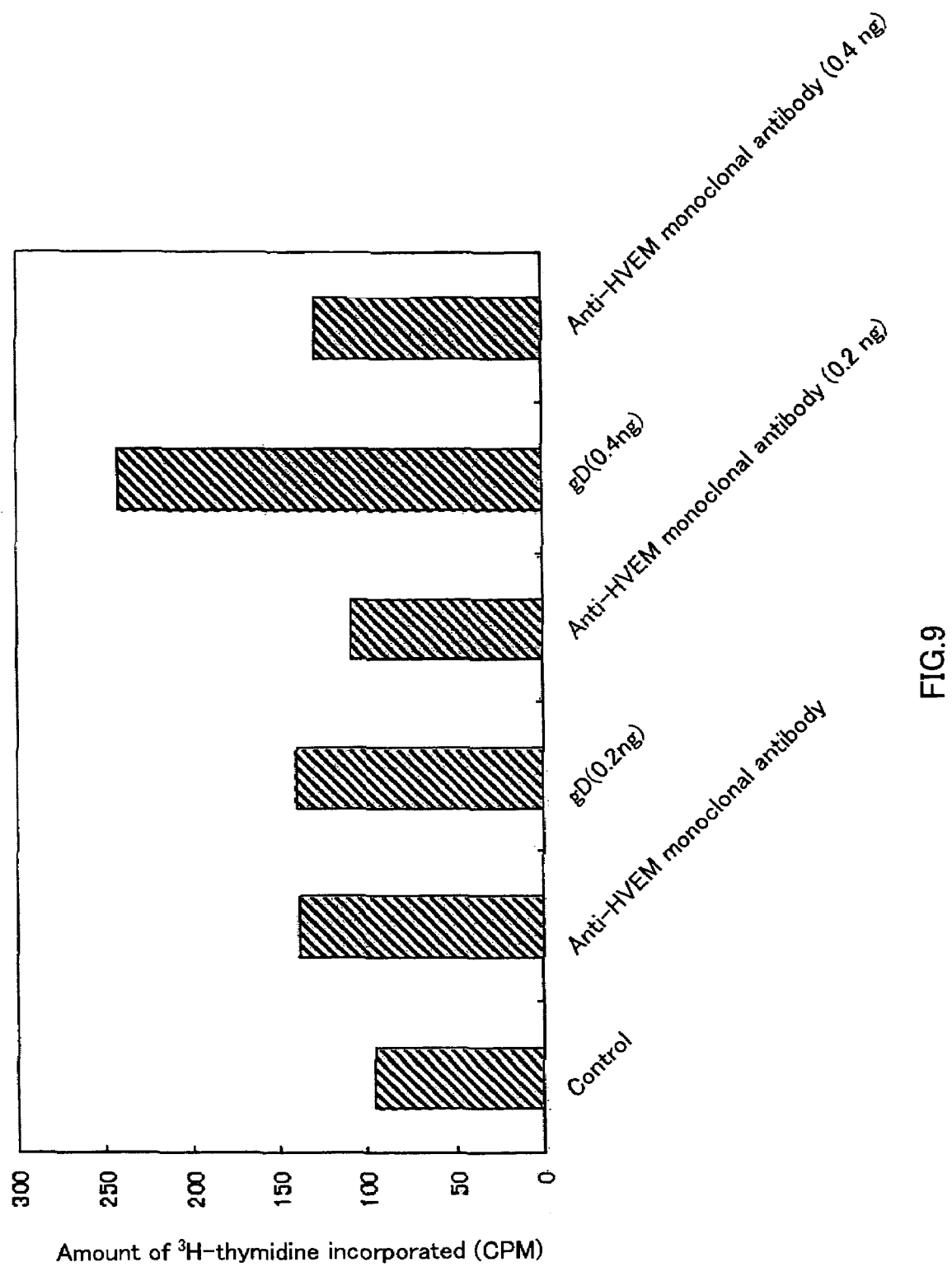
FIG. 9 shows inhibition of HSV-1gD-induced T cell activation action by an anti-HVEM monoclonal antibody.

Mouse T cells were separated using the same method as that used in Example 7. T cells were plated at 6×10$^4$ cells/well and cultured for 5 days in the presence or absence (control) of HSV-1 gD (0.2 or 0.4 ng) and/or anti-HVEM monoclonal antibody (0.01 ng/ml; provided by Dr Patricia G. Spear, Northwestern University, USA). The cultured lymphocytes were labeled with $^3$H-thymidine for about 24 hours and the amount (CPM) of $^3$H-thymidine incorporated was measured using the top counter. The result is shown in FIG. 9. As observed from FIG. 9, although T cells to which 0.4 ng of HSVgD had been added were activated, the activation of T cells was inhibited by the addition of anti-HVEM monoclonal antibody, which blocks HVEM regarded as the receptor for HSVgD, to 0.4 ng of HSVgD. This experiment demonstrated that activation of T cells by HSVgD results from the signaling via the HVEM receptor.

EXAMPLE 9

Figure 10:
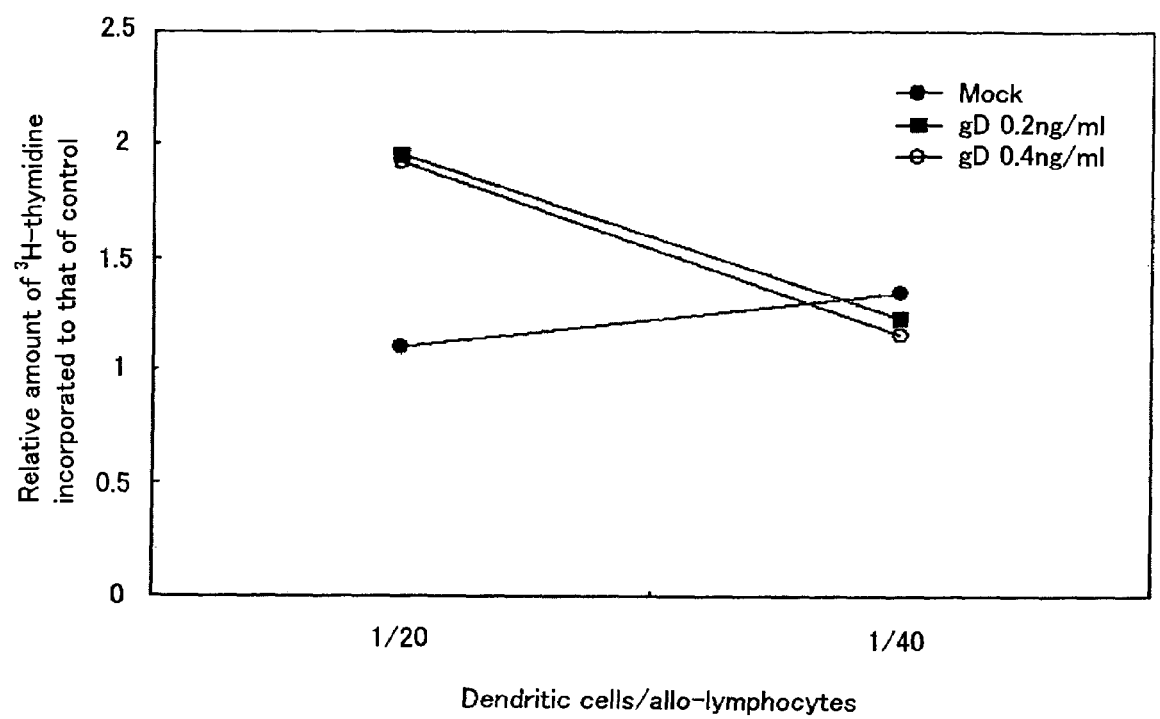
FIG. 10 shows an effect of enhancing the antigen-presenting capability of human dendritic cells by HSV-1gD. In the FIG. 10, DC: Responder represents the ratio of mature dendritic cells to allo-lymphocytes.

Enhancement Effect of Antigen-Presenting Ability of Human Dendritic Cells by HSVgD Immature dendritic cells were obtained from human peripheral blood on day 7 of culture by a method basically similar to that used in Example 5 and supplemented with a medium (control), HSVgD (0.2 ng/ml or 0.4 ng/ml), or mock. This experiment examined the ability of immature dendritic cells with HSVgD (0.2 ng or 0.4 ng) added to them to activate allo-lymphocytes. The CD14-negative fraction of peripheral blood at a concentration of 6×10$^4$ cells as allo-lymphocytes (responders) and mature dendritic cells (DCs) as stimulators whose proliferation had been stopped by irradiation (15 Gy) were co-cultured (the ratio of DCs to responders is 1:20 or 1:40) for 5 days. The cultured lymphocytes were labeled with $^3$H-thymidine at 0.027 Mbq/well for about 12 hours and the amount (CPM: counter per minute) of $^3$H-thymidine incorporated was measured using the top counter. FIG. 10 shows the relative amount of $^3$H-thymidine incorporated by lymphocytes to that of the control after being co-cultured with dendritic cells. As a result, dendritic cells to which HSVgD was added have a higher ability to activate lymphocytes as compared with the control or mock. These results clarified that HSVgD has an effect of enhancing the antigen-presenting ability of human dendritic cells.

EXAMPLE 10

Activation of Human Lymphocytes by HSVgD

Figure 11:
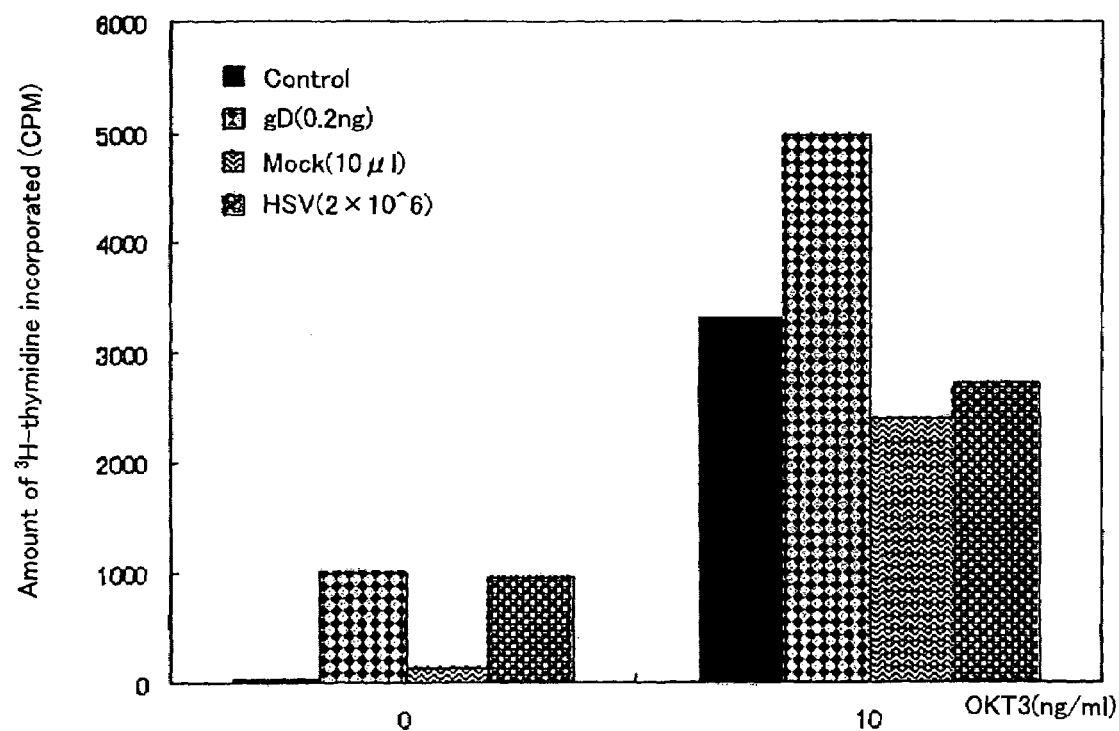
FIG. 11 shows human lymphocyte activation by HSVgD.

The CD14-negative fraction of peripheral blood was obtained by separation and removal of the CD14-positive subset from human peripheral blood by the immunomagnetic bead method. Specifically, a magnetic bead-coupled monoclonal antibody (20 µl/$10^7$ cells) against CD14 antigen was incubated with the cells at 4° C. for 15 min. The CD14-negative fraction of peripheral blood was obtained by magnetic separation and removal of bead-bound cells using a magnetic cell separation system (MACS). Lymphocytes in this peripheral blood were plated at $6\times10^4$ cells/well as allo-lymphocytes (responder), supplemented with OKT3 (0 or 10 ng/ml) as a stimulatory molecule of T cell receptors, and further, with either the inactivated HSV-1 KOS strain (infection efficiency before inactivation: $2\times10^6$PFU), gD (0.2 ng/ml), or mock (10 µl) as a costimulatory molecule, and cultured. On day 6 of culture, the cultured lymphocytes were labeled with $^3$H-thymidine (0.027 Mbq/well) for about 12 hours, and then the amount (CPM) of $^3$H-thymidine incorporated was measured by the top counter. The result is shown in FIG. 11. These results indicated that T cells are not activated in the absence of an anti-CD3 monoclonal antibody OKT3 and that human lymphocytes can be activated in the co-presence of gD and OKT3 (10 ng/ml). It can be thus considered that, like the experiment with mice (Example 7), HSVgD can activate T cells as a costimulatory factor in humans as well.

INDUSTRIAL APPLICABILITY

According to the present invention, antitumor agents, tumor immunity inducers, T cell activators, and dendritic cell activators, extremely safe and capable of inducing an antitumor immune reaction enabling immunotherapy for cancer in such a way that the antitumor effect on a human distant tumor such as metastatic tumors can be exerted. These antitumor agents, tumor immunity inducers, etc. are expected to have broad applications to cancer therapy.

The invention claimed is:

1. A method for treating a tumor, comprising administering a composition comprising a purified glycoprotein antitumor agent directly to a tumor tissue, wherein the purified glycoprotein antitumor agent comprises herpes simplex virus glycoprotein D.

2. A method for treating a distant tumor, such as a metastatic tumor, comprising administering a purified glycoprotein antitumor agent directly to a tumor tissue of a tumor located at a different site than said distant tumor, the tumor and the distant tumor originating from a same tumor, wherein the purified glycoprotein antitumor agent comprises herpes simplex virus glycoprotein D.

3. The method of claim 1 wherein said purified glycoprotein antitumor agent consists of herpes simplex virus glycoprotein D.

4. The method of clam 1 wherein said method comprises multiple injections of said composition comprising the purified glycoprotein antitumor agent.

* * * * *